United States Patent

Böhm et al.

[11] 4,026,944
[45] May 31, 1977

[54] PROCESS FOR MANUFACTURING DIAMINONAPHTHALENE

[75] Inventors: Walter Böhm, Leverkusen; Heinz Ulrich Blank, Odenthal; Guido Skipka, Leverkusen; Friedrich Durholz, Remscheid, all of Germany

[73] Assignee: Bayer Aktiengesellschaft, Leverkusen, Germany

[22] Filed: July 9, 1975

[21] Appl. No.: 594,490

[30] Foreign Application Priority Data

Aug. 10, 1974 Germany ............... 2438542
Nov. 2, 1974 Germany ............... 2452015

[52] U.S. Cl. ............... 260/580; 252/447; 252/459; 252/460; 252/439; 252/443; 252/466 R; 260/575

[51] Int. Cl.² ............... C07C 85/11

[58] Field of Search ............... 260/580, 575

[56] References Cited

UNITED STATES PATENTS

| | | | |
|---|---|---|---|
| 2,894,036 | 7/1959 | Graham | 260/580 |
| 3,213,141 | 10/1965 | Graham et al. | 260/580 |
| 3,232,989 | 2/1966 | Graham | 260/580 |
| 3,499,034 | 3/1970 | Gonzalez | 260/580 |
| 3,832,401 | 8/1974 | Knifton et al. | 260/580 |
| 3,903,167 | 9/1975 | Knifton et al. | 260/580 |
| 3,906,045 | 9/1975 | Knifton et al. | 260/580 |

*Primary Examiner*—Arthur P. Demers
*Attorney, Agent, or Firm*—Burgess, Dinklage & Sprung

[57] ABSTRACT

Diamino naphthalene having the formula

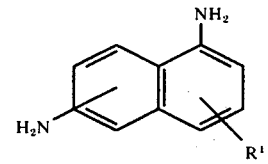

wherein R¹ is hydrogen or amino is prepared by treating dinitro naphthalene having the formula

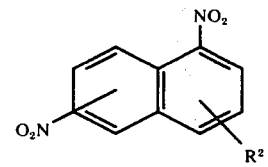

wherein R² is hydrogen or nitro
with hydrogen in the presence of hydrogenation catalysts and organic solvents having the formula

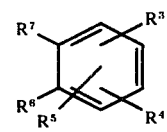

wherein
R³ is hydrogen, halogen or alkyl;
R⁴ is hydrogen, halogen, alkyl, hydroxy, alkoxy, amino, alkylamino, or dialkyl amino;
R⁵ is hydrogen, chlorine, alkyl, hydroxy, alkoxy, amino, alkylamino or dialkyl amino;
R⁶ and R⁷ are the same or different and are either hydrogen or alkyl or together form a —(CH₂)₄ group, optionally substituted once or several times by methyl and/ethyl.

16 Claims, No Drawings

PROCESS FOR MANUFACTURING DIAMINONAPHTHALENE

BACKGROUND

The invention relates to a process for the manufacture of diamino naphthalene by catalytic hydrogenation of dinitro naphthalene.

It is already known to reduce dinitro naphthalenes by catalytic hydrogenation in some organic solvents such as ethanol, dioxane, nitrobenzene (Beilstein, Vol. 13, III. Erg.Werk, 390, 398), but the known processes have not yet found industrial application. The reduction of dinitro naphthalenes to diamino naphthalenes by catalytic hydrogenation is a problem not yet solved as regards use on an industrial scale.

SUMMARY

According to the present invention, diamino naphthalene of the formula

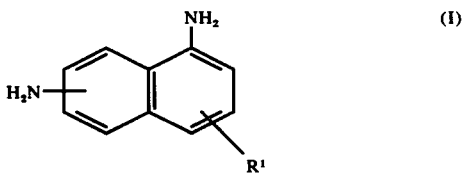

wherein R¹ represents hydrogen or the amino group, is obtained when dinitro naphthalene of the formula

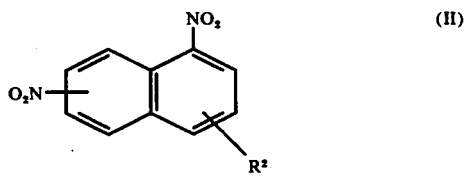

wherein R² represents hydrogen or the nitro group is treated with hydrogen in the presence of hydrogenation catalysts and organic solvents of the formula

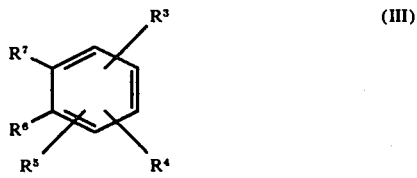

wherein
R³ represents hydrogen, halogen or alkyl,
R⁴ represents hydrogen, halogen, alkyl, an hydroxy group or alkoxy group or an amino group, alkylamino group or dialkyl amino group and
R⁵ represents hydrogen, chlorine, alkyl, an hydroxy group or alkoxy group, an amino group, alkylamino group or dialkyl amino group, and
R⁶ and R⁷ are the same or different and stand for either hydrogen or alkyl or together for a —(CH₂)₄ group optionally substituted once or several times by methyl and/or ethyl.

As halogen there may be mentioned fluorine, chlorine, bromine, iodine, but preferably chlorine.

DESCRIPTION

As examples of suitable alkyl groups there may be mentioned the straight-chain and branched alkyl groups with up to 6, preferable 4 carbon atoms. There may be mentioned, for example, isomers as well as hexyl and pentyl groups, butyl, isobutyl, tert.-butyl, propyl, isopropyl and in particular ethyl and methyl.

In general, the alkyl parts of the alkoxy, alkyl amino and dialkyl amino groups have the same meaning. As examples of suitable solvents of the formula (III) there may be mentioned for example: benzene, toluene, o-, m- and p-xylene, ethyl benzene, o-, m- and p-diethyl benzene, cumol, o-, m-, and p-diisopropyl benzene, 1,2,3-, 1,2,4-, and 1,3,5-triisopropyl benzene, o-, m- and p-ethyl toluene, tetraline, α and β methyl tetraline and α and β ethyl tetraline; chlorobenzene, O-, m- and p-dichloro benzene, trichloro benzenes such as 1,2,4-trichloro benzene, o-, m- and p-chloro toluene, dichloro toluenes such as 2,4-, 3,4-, 2,5- and 2,6-dichloro toluene; phenol, anisol, phenetol, alkoxy toluenes (tolyl ether); o-, m- and p-chlorophenol, dichloro phenols, such as for example 2,4- and 2,5-dichloro phenol; aniline, N-methyl-aniline, N,N-dimethyl aniline, monoalkyl aniline, dialkyl aniline, trialkyl aniline, and tetralkyl aniline, o-, m- and p-toluidine, xylidines, diamino toluenes, anisidine, phenetidine.

Isomers and isomer mixtures not individually mentioned in the aforegoing can also of course be used as solvents of the formula (III).

Mixtures of different solvents of the formula (III) can also of course be employed.

In view of working up the resultant reaction mixture, for example, it may also be advantageous to employ the solvents of the formula (III) in admixture with methanol or water.

In general the amount used of the solvents of the formula (III) or their mixtures is such as to result in a 5 – 40% by weight, preferably 10 – 30 and especially 20 – 25% by weight solution and/or suspension of the dinitro naphthalene of the formula (II). It is also possible to use more or less of the solvent of the formula (III); however, this generally offers no advantage.

The dinitro naphthalenes of the formula (II), which are used as starting compounds in the process according to the invention, are known (BIOS-Final Report, 1152, 43 – 48; DAS No. 1 618 109; DOS No. 1 518 225; DOS No. 1 643 059; DOS No. 1 150 965; DAS No. 1 179 545; U.S. Pat. No. 3,326,983; Houben-Weyl, X, 493 – 495).

The process of the invention can be particularly advantageously employed to effect reduction of 1,5- and 1,8-dinitro naphthalene to the corresponding diamino naphthalenes, particularly if mixtures of nitro naphthalenes constitute the starting material whose content of 1,5- and 1,8-dinitro naphthalene is over 90, especially 95% by weight.

Possible hydrogenation catalysts are the known hydrogenation catalysts (cf. Houben-Weyl, Methoden der organischen Chemie, Vol. IV/2, 5, 163 – 192 (1955)); preferred are the metals of Group VIII of the periodic system: iron, cobalt, nickel, ruthenium, rhodium, palladium, osmium, iridium, platinum which can also be used for example in the form of their oxides, sulphides and halogenides; in particular the metals of the platinum and palladium group can be used, such as osmium, iridium, platinum, ruthenium, rhodium and palladium;

in particular platinum and palladium themselves may be used.

The aforementioned metals or their oxides, sulphides and halogenides can also of course be used in the form of supported catalysts; suitable for this purpose are the known catalyst carriers, such as the carbonates and sulphates of alkaline earth metals, e.g. barium carbonate, barium sulphate, calcium carbonate and calcium sulphate, also alumina, aluminium oxide, silicon dioxide, and silicic acids. Carbon, particularly in the form of activated charcoal, is preferred as a catalyst carrier.

In general, the amount of catalyst is 0.005 – 0.5, preferably 0.01 – 0.1 and especially 0.02 – 0.05% by weight of metal based on the amount of nitro compound used.

If a supported catalyst is employed, the amount to be used is calculated on the basis of its metal content in accordance with the above details relating to the catalyst amount. Supported catalysts are preferably used with a content of catalyst metal of 0.1 to 5.0% by weight, in particular platinum/charcoal.

When performing the process of the invention the choice of suitable solvent or solvent mixture may depend on the purity of the starting material.

If the starting material only contains small amounts of impurities, for example after prior recrystallization, it is particularly advantageous to use alkylated benzenes, in particular toluene and xylene.

With increasing amounts of impurities it may be advisable to use other solvents of the formula (III) in admixture with or instead of alkylated benzenes. There may be preferably mentioned: chlorobenzenes, anilines, toluidine, N,N-dimethyl-aniline, anisol and substituted anisols.

The solvent or solvent mixture best suited to reduce the chosen starting material can be easily determined, if desired, by carrying out a few preliminary tests.

Since the reaction is exothermic, it is generally expedient to work in a temperature range between 20° and 180° C, preferably 30° and 100° C and especially between 40° and 80° C; it is possible to exceed the upper limit of 180° C but this usually entails disadvantages rather than any advantages. Large amounts of heat are generated in this reaction which have to be cooled. This is a difficult and costly procedure with the prevailing danger that the reaction will get out of control ultimately causing an explosion.

In general, work is carried out at a hydrogen pressure of up to 50 bars, preferably in the range of 3 – 20, in particular 5 – 15 bars. The reaction time is also pressure-dependent so that rising hydrogen pressure will mean shorter reaction times; however this advantage is outweighed by the problems relating to apparatus which can arise at elevated hydrogen pressure. In general, the reaction time depends on a variety of factors so that it is not possible to make any general statement about its duration; the factors which influence it are the type and amount of the chosen solvent, type and amount of the chosen catalyst, hydrogen pressure and temperature. In general, the end of the reaction can be ascertained in accordance with known methods from the cessation of further hydrogen absorption; to establish whether conversion of the starting compounds is complete, it is particularly advantageous to take samples continuously or discontinuously and to analyze them according to known methods, such as gas chromatography.

In general, the process of the invention is performed in the following manner.

The dinitro compound, the chosen solvent and the catalyst are introduced into the appropriate apparatus and constantly mixed well, for example by stirring, at the chosen hydrogen pressure. The reaction mixture is brought by heating to the required reaction temperature; heating is stopped as soon as the reaction produces enough of its own heat due to the exothermic reaction. The reaction temperature is thereafter kept at a constant level by cooling. It is possible that an aqueous phase may form in the course of the reaction due to the water of reaction which forms in the reaction mixture.

The reduction of dinitro naphthalenes of the formula (I) proceeds as is well known with the formation of water in accordance with the following reaction equation which is given by way of illustrating 1,5-dinitro naphthalene:

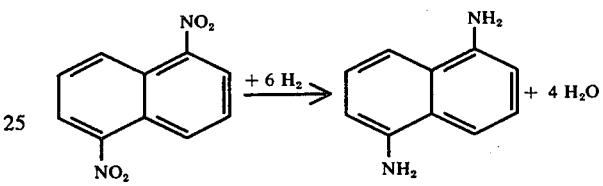

In general, the catalyst employed is moistened with water in order to preclude with certainty catalysis of the explosive reaction of hydrogen with oxygen by the catalyst when charging and filling the apparatus with hydrogen. The small amounts of water introduced at the same time interfere in those cases in which the solvent of the formula (III) is not already used in admixture with water as little as does the water of reaction which forms.

The hydrogen used in the reaction can be introduced in the usual manner. Hydrogen can either be introduced continuously and work hence performed at a constant hydrogen pressure, or discontinuously whereby after any fall in hydrogen pressure this is restored to its original value or another value.

In either case the end of the reaction is evident from the cessation of hydrogen consumption which can be ascertained by the usual, physical methods.

After completion of the reaction, the reaction mixture is worked up in the usual manner. For example, after releasing pressure and cooling, the catalyst can be filtered off whilst still at an elevated temperature of about 30° to 100° C, preferably 40° to 60° C. This step can also be advantageously performed at a temperature at which — depending on the nature and amount of the selected solvent — none of the amine obtained as the reaction product has as yet crystallized out. It may likewise be expedient and possibly advantageous, e.g. when reducing 1,5- and 1,8-dinitro naphthalene mixtures, to separate off the amine (1,5-diamino naphthalene) which is scarcely soluble and crystallizes out at higher temperatures, together with the catalyst and then to effect separation from the catalyst in the usual way, e.g. by dissolving in a solvent, and finally to carry out isolation, whilst the amine (1,8-diamino naphthalene) left in the reaction solution is isolated from the solution in the usual manner, e.g. by crystallizing at lower temperatures and separating (filtrating, centrifuging), or removing the solvent from the solution, e.g. by distillation.

The water produced in the reaction can be separated from the organic reaction phase, optionally together with the water admixed with the solvent of the formula (III), providing water forms its own aqueous phase; said separation can be effected in the usual manner, e.g. prior to separation of the catalyst; however, the water may also be removed together with the solvent upon isolation of the reaction product.

The amine obtained as the reaction product can be isolated in the usual manner, for example by crystallizing or expediently by distilling off the solvent; it can also be isolated in the usual manner by converting it into a corresponding ammonium salt. Purification of the amine or of the ammonium salt produced therefrom in the usual manner for the purpose of isolating and/or purifying can proceed in the normal way, e.g. by distillation or recrystallization.

The process of the invention constitutes a particularly advantageous means of reducing dinitro naphthalenes of the formula (II) to the corresponding diamino naphthalenes of the formula (I) by catalytic hydrogenation. It is an improvement over the prior art in that work can be performed with a higher concentration and a smaller amount of catalyst, i.e. greater space/-time yield; in addition, there is practically no or only very little lessening in the activity of the catalyst, particularly when using unpurified starting material, whilst rapid lessening is sometimes to be observed in previously employed solvents, such as alochols (cf. Examples 2, 7).

The process according to the invention has the particular advantage over the usual reduction processes with metallic iron (BIOS-Final Report 1152, item No. 22, pages 48–54) that easily accessible hydrogen instead of metallic iron serves as the reducing agent and that the formation of iron oxides is avoided.

The amino naphthalenes are known intermediate products for the production of corresponding isocyanates and of dyestuffs.

The following Examples illustrate the invention:

EXAMPLES 1 – 4

A dinitro naphthalene was used as the starting material which contained 97.7% by weight of 1,8-dinitro naphthalene and, in addition to 7 other non-identified impurities, less than 0.1% by weight of 1,5-and 1,3-dinitro naphthalene. In each instance, 22 g of this starting material were catalytically hydrogenated, in a 0.7 liter stirrer autoclave, in 300 ml of solvent by discontinuously introducing hydrogen under pressure. After completion of hydogenation, the catalyst was filtered off and the reaction product precipitated with 300 ml of 36% by weight of hydrochloric acid as dihydrochloride and then filtered off (method A), or alternatively the catalyst filtered off and the reaction product recovered by distilling off the solvent and recrystallizing the residue from a mixture of methanol and water in a ratio of 3 : 1 (method B). The resultant 1,8-diamino naphthalene and its dihydrochloride were dried at 20° C/200 mm Hg.

The type of solvent, type and amount of catalyst, reaction temperature, hydrogen pressure during the reaction, working-up method, yield and purity of the crude product as well as the calculated pure yield in % of the theory are all given in Table I.

TABLE I

| Example No. | Solvent | Catalyst | Reaction Temp. ° C | H₂ pressure bar | Reaction time (hrs) | Processing method | 1,8-diaminonaphthalene g (% purity) % of theory | |
|---|---|---|---|---|---|---|---|---|
| 1. | isopropanol | 2g 0.5% wt. Pd/act.char. | 50–100 | 10–30 | 26.5 | A | 21(82) | 76 |
| 2. | isopropanol | 1g 1.0% wt. Pt/act.char. | 50–100 | 10–20 | 20 | | incomplete conversion and cessation of reac. | |
| 3. | aniline | " | 30–40 | 10–20 | 4 | A | 22.5(78) | 78 |
| 4. | toluene | " | 30–40 | 10–20 | 1.5 | B | 14.6(97.6) | 93 |

*comparison example

EXAMPLES 5 – 7

A dinitro naphthalene was employed as the starting material which had a content of 97.3% by weight of 1,8-dinitro naphthalene and less than 0.1% by weight of each of the following impurities: 1,5- and 1,3-dinitro naphthalene, 1,3,8-trinitronaphthalene, 1,4,5-trinitronaphthalene, 1,3,5-trinitronaphthalene, 1,7-dinitro naphthalene, 1,6-dinitro naphthalene, 1,4-dinitro naphthalene, α-nitro-naphthalene. As in Examples 1 to 4, 22 g each of the starting material were catalytically hydrogenated in 75 ml of solvent. After completion of the reaction the degree of conversion was determined by thin-layer chromatography (benzene/chloroform/ethanol (80/20/5); silica gel). The experimental data are set forth in Table II in a manner analogous with Table I.

TABLE II

| Example No. | Solvent | Catalyst | Reaction Temp. ° C | H₂ pressure (bar) | Reaction time (hrs) | Conversion |
|---|---|---|---|---|---|---|
| 5 | toluene | 1g 1.0% wt. pt/act.char. | 30–50 | 20–50 | 12 | quantitative |
| 6 | toluene/methanol (1:1) | " | 30–50 | 20–50 | 12.5 | quantitative |
| 7* | methanol | " | 30–50 | 20–50 | 12 | cessation of reaction after less than 80 % conversion |

*comparison example

EXAMPLE 8

88 g of the dinitro naphthalene employed in Examples 5 to 7 were hydrogenated, in a 0.7 liter stirrer autoclave, in 300 ml of toluene in the presence of 4 g of 1% by weight catalyst of platinum and activated charcoal at a temperature of 50° C and a constant hydrogen pressure of 10 bars. Hydrogenation was completed after 5½ hours. The reaction solution was filtered off from the catalyst and the solvent distilled off. The residue was taken up in 70 ml of methanol and introduced into a mixture of 80 g of ice and 80 g of concentrated hydrochloric acid. The solids were rapidly filtered off under suction and dried at 50° C/200 mm Hg.

The yield was 85.2 g of 1,8-diamino naphthalene-dihydrochloride of 95% strength purity; this corresponds to a yield of about 92% of the theory.

EXAMPLE 9

88 g of dinitro naphthalene with a content of 89.8% by weight of 1,8-dinitro naphthalene, 7.8% by weight of 1,5- and 1,3-dinitro naphthalene, less than 0.1% by weight each of 1,3,8- , 1,4,5- , 1,3,5-trinitronaphthalene, 1,7- , 1,6- and 1,4-dinitro naphthalene, α-nitronaphthalene as well as less than 0.4% by weight of other unknown impurities, were hydrogenated, in a 0.7 liter stirrer autoclave, in 300 ml of toluene in the presence of 4 g of 1% by weight catalyst of platinum on activated charcoal, at a temperature of 50° C and a constant hydrogen pressure of 10 bars. Hydrogenation was completed after 10 hours, the reaction solution was filtered off from the catalyst and fractionally distilled in vacuo. 49 g of 1,8-diamino naphthalene of 98–99% purity were obtained in the boiling range 140°–142° C at a pressure of 0.2 mm Hg; this corresponds to a yield of 86% of the theory.

The higher-boiling distillation residue of 7 g was revealed by thin-layer chromatography to contain more than 90% of 1,8-diamino naphthalene so that the total yield corresponded to about 97% of the theory.

EXAMPLES 10–14

The dinitro naphthalene employed as the starting material contained 96.6% by weight of 1,8-dinitro naphthalene, less than 0.1% by weight each of 1,5- and 1,3-dinitro naphthalene, 1,3,5-trinitroanphthalene, 1,7- , 1,6- , 1,4-dinitro naphthalene, α-nitro-naphthalene. 22 g each of dinitro naphthalene were hydrogenated, in a 0.3 liter stirrer autoclave, in the presence of 1 g of 1% strength catalyst of platinum on activated charcoal, at a temperature of 70° C and a hydrogen pressure of 9 – 10 bars. After completion of hydrogenation the reaction solution was filtered off from the catalyst, the solvent distilled and the residue taken up in 70 ml of methanol and introduced into a mixture of 80 g of ice and 80 g of concentrated hydrochloric acid. The precipitated diamino naphthalene dihydrochloride was filtered and dried at 50° C/200 mm Hg.

Type and amount of solvent employed, reaction time, purity and yield of reaction product in g and yield of 1,8-diamino naphthalene in % of the theory are set forth in the following Table III.

TABLE III

| Example No. | Solvent | Reaction time (hrs) | 1,8-diamino naphthalene dihydrochloride | | |
|---|---|---|---|---|---|
| | | | Yield (g) | Purity (%) | Yield (% of the theory) |
| 10 | 75 ml chlorobenzene | 6 | 20.3 | 93 | 85 |
| 11 | 75 ml o-dichlorobenzene | 2.5 | 20.9 | 91 | 86 |
| 12 | 75 ml N,N-dimethyl aniline | 5.5 | 20.2 | 91 | 83 |
| 13 | 150 ml phenol | 20 | gas chromatographic analysis: 88 % of 1,8-diamino naphthalene | | |
| 14 | 150 ml anisol | 14 | 20.6 | 96 | 89 |

EXAMPLES 15 and 16

A starting material was used containing 63.8% by weight of 1,8-dinitro naphthalene and 34.4% by weight of 1,5-dinitro naphthalene and at least 8 detectable impurities each of not more than 0.2% by weight. 150 g each of starting material were hydrogenated, in a 1.3 liter stirrer autoclave, in the presence of 7 g of 1% by weight catalyst of platinum on activated charcoal, at a temperature of 50° to 70° C and a hydrogen pressure of 9 – 10 bars. After completion of hydrogenation, the reaction solution was filtered off from the catalyst and from the precipitated 1,5-diamino naphthalene. The filtrate was freed from the solvent by distillation and the residue analyzed by gas chromatography. The precipitated 1,5-diamino naphthalene was dissolved in dimethyl formamide, filtered off from the catalyst and recovered by subsequent crystallization.

Solvents and yields are set forth in Table IV.

TABLE IV

| Example No. | Solvent | Reac-* tion time (hrs) | Yields** | | | |
|---|---|---|---|---|---|---|
| | | | 1,5-diamino naphthalene | 1,8-diamino-naphthalene | Analysis | % of theory (found) |
| 15 | 525 ml toluene | 1.5 | 35.4 g*** | 70.6 g | 98.2% 1,8-DAN 0.7% 1,5-DAN | 95% 1,5-DAN 100% 1,8-DAN |
| 16 | 525 ml N,N-dimethyl aniline | 3.75 | 28.0 g | 83.8 g | 6.6% solvent 81.4% 1,8-DAN 11.9% 1,5-DAN | 100% 1,5-DAN 99% 1,8-DAN |

*The dinitro naphthalene used was reacted quantitatively in the given reaction time
**DAN = diamino naphthalene
***After sublimation In addition, the residue from Example 14 (70.6 g) consisting substantially of 1,8-diamino naphthalene was fractionally distilled at 2 – 3 mm Hg over a 50 cm long silver mirror column 3 cm in diameter which was filled with Raschig rings made of glass 4mm in diameter.

There were obtained:
59.0 g of 1,8-diamino naphthalene of 99% purity, corresponding to 85% of the theory, as the distillate. Melting point: 65° C 35.4 g of 1,5-diamino naphthalene corresponding to 95% of the theory. Melting point: 185°–186° C
4.5 g of product left in the column (89% of 1,8- and 8% of 1,5-diamino naphthalene).
5.0 g of distillation residue (72% of 1,8- and 21% of 1,5-diamino naphthalene).

EXAMPLE 17

60 g (0.275 mol) of 1,5-dinitro naphthalene were suspended, in a 700 ml stirrer autoclave, in 340 ml of aniline and treated with 8 g of water-moist, 5% strength catalyst of palladium on activated charcola, corresponding to 2.8 g of dry catalyst. Hydrogenation was performed at a temperature of about 100° C and an initial hydrogen pressure of about 10 bars. As soon as the hydrogen pressure dropped to 5 bars, the hydrogen supply was stepped up until the original value of 10 bars was reattained. After 104 minutes the hydrogen uptake was finished and the reaction over. The catalyst was separated off at about 70° C by filtration and the filtrate cooled to 20° C whereupon 1,5-diamino naphthalene crystallized out. The crystallate was then filtered off and washed twice with 50 ml of methanol; 24 g of 1,5-diamino naphthalene were obtained with a m.p. of 189°–190° C.

The mother liquor was combined with the washing methanol and methanol and aniline distilled off from this solution by means of water vapour distillation. On cooling to 20° C a further 16 g of 1,5-diamino naphthalene of m.p. 188°–189° C crystallized out of the remaining aqueous solution.

The total yield was 40 g (91.9% of the theory) of 1,5-diamino naphthalene.

EXAMPLE 18

60 g (0.275 mol) of 1,5-dinitro naphthalene were suspended, in a 700 ml stirrer autoclave, in 340 ml of aniline and treated with 18 g of water-moist, 1%-strength catalyst of platinum and activated charcola corresponding to 8 g of dry catalyst. Hydrogenation was carried out at 50° C and a hydrogen pressure of 10 bars, as was described in Example 1. The hydrogen uptake was finished after 2 hours. The catalyst was separated off by filtration at 80° C and the aniline subsequently removed by water-vapour distillation. The distillation residue was cooled to 18° C and the precipitated crystallate filtered off and dried. In this way 40 g (92% of the theory) of 1,5-diamino naphthalene of m.p. 188°–189° C were obtained.

EXAMPLE 19

60 (0.275 mol) of 1,5-dinitro napahtlene were hydrogenated, as described above, in 340 ml of aniline in the presence of 8 g of a moist, 5% catalyst of palladium on activated charcoal, corresponding to 2.8g of dry catalyst at a hydrogen pressure of 40 – 50 bars and a temperature of 80° C. After filtering off the catalyst at 80° C and cooling the filtrate to 18° C, 36 g (85.6% of the theory) of 1,5-dinitro naphthalene of m.p. 183°–184° C were obtained.

EXAMPLE 20

60 g (0.275 mol) of 1,8-dinitro naphthalene were hydrogenated, as described above, in 340 ml of o-toluidine in the presence of 10 g of water-moist, 5% catalyst of palladium on activated charcoal, corresponding to 3.5 g of dry catalyst, at 100° C and a hydrogen pressure of 10 bars. The reaction was over after 70 minutes.

After separating off the catalyst by filtrating at 80° C and distilling off the o-toluidine in vacuo, 39.5 g (90.9% of the therory) of ccrude 1,8-naphthyelone diamine were obtained.

EXAMPLE 21

60 g of technical 1,8-dinitro naphthalene consisting of 42.2 g of 1,8-dinitro naphthalene, 4.5 g of 1,5-dinitro naphthalene, 3 g of isomeric dinitro naphthalenes and 17.1 g of water, were hydrogenated, as described above, in 340 ml of aniline in the presence of 8 g of a moist, 5% catalyst of palladium on activated charcoal corresponding to 2.8 g of dry catalyst, at 100° C and a hydrogen pressure of 10 bars. The hydrogen uptake was finished after 74 minutes. After filtering off the catalyst at 60° C, the water from the reaction, and the aniline were distilled off in vacuo. 42 g of crude 1,8-naphthylene diamine were then left. During subsequent distillation in vacuo of the crude product, 27 g of a 1,8-naphthylene diamine fraction distilling over at 170°–190° C C/3 mm Hg were obtained corresponding to a yield of 88.2% of the theory, based on 42.2 g of 1,8-dinitro naphthalene. The m.p. of the 1,8-naphthylene diamine thus obtained was 60.5° C.

What is claimed is:
1. A process for preparing a diamino naphthalene having the formula

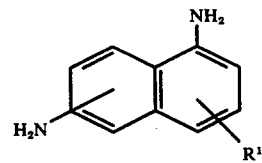

wherein $R^1$ is hydrogen or amino which comprises contacting a dinitro naphthalene having the formula

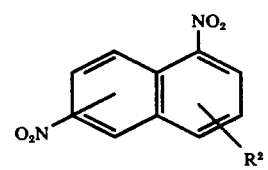

wherein $R^2$ is hydrogen nitro with hydrogen in the presence of a heterogeneous hydrogenation catalyst and an organic solvent selected from the group consisting of benzene, toluene,o- , m- and p-xylene, ethylbenzene, o-, m- and p-diethylbenzene, cumol, o-, m-, and p-diisopropylbenzene, 1,2,3-, 1,2,4- and 1,3,5-triisopropylbenzene, o-, m- and p-ethyl toluene, tetraline, $\alpha$ and $\Delta$ methyl tetraline and $\alpha$ and $\Delta$ ethyl tetraline, chlorobenzene, o-, m- and p-dichlorobenzene, a trichlorobenzene, o-, m- and p-chlorotoluene, a dichlorotoluene, phenol anisol, phenetol, an alkoxytoluene, o-, m- and p-chlorophenol, a dichlorophenol, analine, N-methyl anilene, a tri alkyl aniline, a tetra alkyl aniline, o-, m- and p-toluidine a xylidine, a diamino toluene, phenetidine and anisidine, the amount of solvent being present such that there results a 5 to 40% by weight solution or suspension of said dintro naphthalene compound.
2. A process according to claim 1 wherein the hydrogenation is carried out in a 10–30% by weight solution or suspenion of dinitro naphthalene compound.
3. A process according to claim 1 wherein hydrogenation is carried out in a 20–25% by weight solution or suspension of dinitro naphthalene.

4. A process according to claim 1 wherein hydrogenation is carried out employing toluene as the solvent.

5. A process according to claim 1 wherein the hydrogenation is carried out employing aniline as the solvent.

6. A process according to claim 1 wherein the hydrogenation is carried out employing N,N-dimentyl aniline as the solvent.

7. A process according to claim 1 wherein the hydrogenation is carried out in the presence of a water phase.

8. A process according to claim 1 wherein a skeleton caatalyst is employed for the hydrogenation.

9. A process according to claim 8 wherein the skeleton catalyst is a nickel and/or iron containing catalyst.

10. A process according to claim 1 wherein a supported catalyst is is employed as the hydrogenation catalyst.

11. A process according to claim 10 wherein the supported catalyst is a phatinum or palladium containing support catalyst.

12. A process according to claim 11 wherein the catalyst is a platinum on charcoal catalyst.

13. A process according to claim 11 wherein the catalyst is a palladium on charcoal catalyst.

14. A process according to claim 1 wherein the catalyst is present in an amount of 0.005 to 0.5% by weight of metal based upon the weight of said nitro naphthalene compound.

15. A process according to claim 1 wherein the catalyst is present in an amount of 0.01 to 0.1% by weight of metal based upon the weight of nitro naphthalene compound.

16. A process according to claim 1 wherein the catalyst is present in an amount of 0.02 to 0.05% by weight of metal based upon the weight of said nitro napthalene compound.

* * * * *

UNITED STATES PATENT AND TRADEMARK OFFICE
CERTIFICATE OF CORRECTION

PATENT NO. : 4,026,944
DATED : May 31, 1977
INVENTOR(S) : Walter Böhm et al

It is certified that error appears in the above-identified patent and that said Letters Patent are hereby corrected as shown below:

Claim 1 is incorrectly printed and should read as follows:

1. A process for preparing a diamino naphthalene having the formula

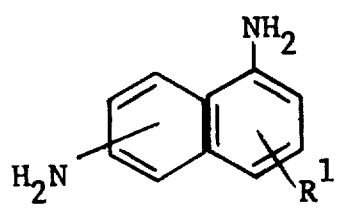

wherein $R^1$ is hydrogen or amino which comprises contacting a dinitro naphthalene having the formula

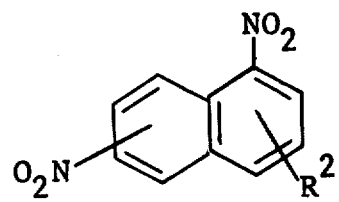

wherein $R^2$ is hydrogen or nitro with hydrogen in the presence of a heterogeneous hydrogenation catalyst and an organic solvent selected from the group consisting of benzene, toluene, o-, m- and p-xylene, ethylbenzene, o-, m- and p-diethylbenzene, cumol, o-, m- and p-diisopropylbenzene, 1,2,3-, 1,2,4- and 1,3,5-triisopropylbenzene, o-, m- and p-ethyl toluene, tetraline, α and β methyl tetraline and α and β ethyl tetraline, chlorobenzene, o-, m- and p-dichlorobenzene, a trichlorobenzene, o-, m- and p-chlorotoluene, a dichlorotoluene, phenol, anisol, phenetol, an

UNITED STATES PATENT AND TRADEMARK OFFICE
CERTIFICATE OF CORRECTION

PATENT NO. : 4,026,944  Page 2 of 2 pages
DATED : May 31, 1977
INVENTOR(S) : Walter Böhm et al It is certified that error appears in the above-identified patent and that said Letters Patent are hereby corrected as shown below:

alkoxytoluene, o-, m- and p-chlorophenol, a dichlorophenol, aniline, N-methyl aniline, N,N-dimethyl aniline, a mono alkyl aniline, a dialkyl aniline, a tri alkyl aniline, a tetra alkyl aniline, o-, m- and p-toluidine, a xylidine, a diamino toluene, phenetidine and anisidine, the amount of solvent being present such that there results a 5 to 40% by weight solution or suspension of said dinitro naphthalene compound.

Claim 6, line 2, "dimentyl" should read -- dimethyl --.

Claim 11, line 2, "phatinum" should read -- platinum --.

Column 9, line 12, "charcola" should read -- charcoal --.
line 52, "naphahtlene" should read -- naphthalene --.

Column 10, line 3, "ccrude" should read -- crude --.
line 3, "naphthyelone" should read -- naphthalene --.

Signed and Sealed this

First Day of November 1977

[SEAL]

Attest:

RUTH C. MASON
*Attesting Officer*

LUTRELLE F. PARKER
*Acting Commissioner of Patents and Trademark*